United States Patent
Anderson et al.

(10) Patent No.: US 8,164,444 B2
(45) Date of Patent: Apr. 24, 2012

(54) POSITION DETECTION

(75) Inventors: Dean S. Anderson, Cologne, MN (US); Danny J. Vatland, Chanhassen, MN (US); Christopher M. Thielen, Maple Grove, MN (US)

(73) Assignee: Healthsense, Inc., Mendota Heights, MN (US)

( * ) Notice: Subject to any disclaimer, the term of this patent is extended or adjusted under 35 U.S.C. 154(b) by 462 days.

(21) Appl. No.: 12/432,565

(22) Filed: Apr. 29, 2009

(65) Prior Publication Data

US 2010/0277309 A1 Nov. 4, 2010

(51) Int. Cl.
*G08B 1/08* (2006.01)

(52) U.S. Cl. .......... 340/539.13; 340/539.11; 340/539.21

(58) Field of Classification Search .............. 340/539.13
See application file for complete search history.

(56) References Cited

U.S. PATENT DOCUMENTS

| | | | |
|---|---|---|---|
| 4,259,548 A | 3/1981 | Fahey et al. | |
| 5,204,670 A | 4/1993 | Stinton | |
| 5,905,436 A | 5/1999 | Dwight et al. | |
| 6,108,685 A | 8/2000 | Kutzik et al. | |
| 6,297,738 B1 | 10/2001 | Newham | |
| 6,524,239 B1 | 2/2003 | Reed et al. | |
| 6,540,674 B2 | 4/2003 | Zadrozny et al. | |
| 6,821,258 B2 | 11/2004 | Reed et al. | |
| 6,950,026 B2 | 9/2005 | Yamashita et al. | |
| 7,141,026 B2 | 11/2006 | Aminian et al. | |
| 7,583,961 B2 * | 9/2009 | Kappes et al. | 455/423 |
| 2002/0198473 A1 | 12/2002 | Kumar et al. | |
| 2003/0043073 A1 * | 3/2003 | Gray et al. | 342/465 |
| 2003/0096590 A1 | 5/2003 | Satoh | |
| 2003/0117279 A1 | 6/2003 | Ueno et al. | |
| 2003/0189485 A1 | 10/2003 | Smith | |
| 2003/0216670 A1 | 11/2003 | Beggs | |
| 2003/0229471 A1 | 12/2003 | Guralnik et al. | |

(Continued)

FOREIGN PATENT DOCUMENTS

DE 19522803 1/1997

(Continued)

OTHER PUBLICATIONS

AIST, "Housing That Protects the Home-Maker—Development of Technology Capable of Detecting Abnormalities in the Ordinary Living Pattern Home-Maker for Information Signaling and Health Management—", http://www.aist.go.jp/aist_e/latest_research/2003/20030221/20030221.html, AIST, 7 pgs., Feb. 3, 2003.

*Primary Examiner* — George Bugg
*Assistant Examiner* — Kerri McNally
(74) *Attorney, Agent, or Firm* — Brooks, Cameron & Huebsch, PLLC

(57) ABSTRACT

Embodiments of the present disclosure relate to methods, devices, and systems for position detections of an individual. One method to detect a position of an individual includes creating a zone map by mapping locations of a number of fixed sensors in a zone and signal strengths of a number of communications between the fixed sensors and at least two wireless access points. The method also includes determining signal strength values of a number of communications between the wireless access points and a mobile sensor and comparing the signal strength values of the number of communications between at least two wireless access points and the mobile sensor with the zone map to determine the mobile sensor's position in relation to the zone.

20 Claims, 8 Drawing Sheets

U.S. PATENT DOCUMENTS

| | | |
|---|---|---|
| 2005/0057357 A1 | 3/2005 | Helal et al. |
| 2005/0131736 A1 | 6/2005 | Nelson et al. |
| 2005/0137465 A1 | 6/2005 | Cuddihy et al. |
| 2005/0258957 A1 * | 11/2005 | Krumm et al. ........... 340/539.13 |
| 2007/0152811 A1 | 7/2007 | Anderson |
| 2007/0152837 A1 | 7/2007 | Bischoff et al. |
| 2007/0192174 A1 | 8/2007 | Bischoff |
| 2008/0242305 A1 * | 10/2008 | Kahlert et al. ................ 455/440 |

FOREIGN PATENT DOCUMENTS

| | | |
|---|---|---|
| EP | 1571583 | 9/2005 |
| EP | 1585077 | 10/2005 |

* cited by examiner

POSITION DETECTION

BACKGROUND

In the field of remote health monitoring, systems have been developed to enable an individual to contact medical professionals from their dwelling regarding a medical emergency. For example, in various systems, an individual is equipped with an emergency call button that initiates a call or signal to an emergency call center.

The concept of such a system is that if an individual has a health related problem, they can press the emergency call button and emergency medical providers will respond to assist them. However, in some cases, the individual is unable to press the emergency call button, such as when an individual has fallen and cannot reach the button, is rendered unconscious, or is cognitively impaired.

Some systems have been developed that use sensors within the residence to monitor an individual within a dwelling. Typically, these systems include motion sensors, for example, that are connected to a base control system that monitors areas within the dwelling for movement. When a lack of movement is indicated, the system indicates the lack of movement to a remote assistance center that can contact a party to aid the individual. However, not all inactivity indicates that an individual is in need of assistance. For example, an individual can be sitting in a chair for a prolonged period, or lying in bed. These periods may be sufficient to initiate an alert for third party response, but may not actually be an emergency. In some of these systems, the system is designed to allow a third party to intervene to aid the individual according to the analysis of the information received by the remote assistance center.

Some systems also are designed such that the individual being monitored has to actively turn the system on and off (activate/deactivate) when leaving and returning to the dwelling to indicate whether the individual is home or away. This added step can be forgotten in some instances and thereby can cause the system to be ineffective at times.

DETAILED DESCRIPTION OF THE INVENTION

Figure 1:
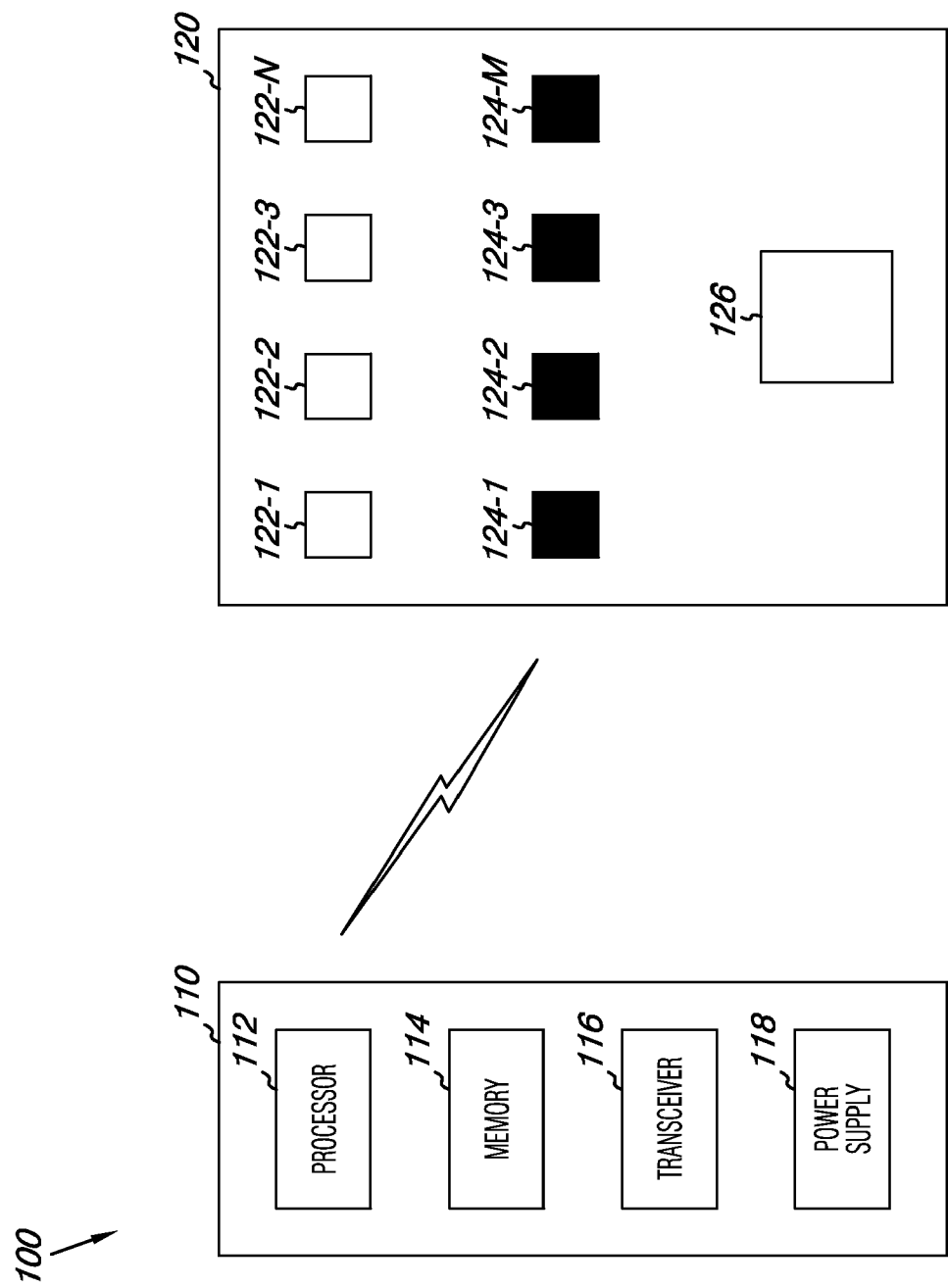
FIG. 1 illustrates an embodiment of a system for detecting the position of an individual according to the present disclosure.

Embodiments of the present disclosure include systems, devices, and methods to detect the position of an individual within a zone, for example, a portion of or an entire house, condominium, townhouse, apartment, or institution (e.g., hospital, assisted living facility, nursing home, prison, etc.)

Embodiments can, for example, provide methods for detecting a position of an individual. For instance, in some embodiments, a zone map can be created by mapping the locations of a number of fixed sensors in a zone and the signal strengths of a number of communications between the fixed sensors and at least two wireless access points, determining signal strength values of a number of communications between the number of wireless access points and a mobile sensor, and comparing the signal strength values of a number of the communications between the at least two wireless access points and the mobile sensor with the zone map to determine the mobile sensor's position in relation to the zone.

Embodiments can include a number of fixed sensors in which the sensors are associated with a variety of components within the zone to indicate the activity of the individual. For example, fixed sensors can be associated with (e.g., connected) to a user's bed to indicate that a client is lying on the bed. Fixed sensors can also be used on drawers and cupboards to indicate when an individual opens a drawer or the door to a cupboard.

Many other types and uses for the fixed sensors are described in more detail below. Such fixed sensors can be used in a position detection system of the present disclosure and as part of a monitoring system that includes a position detection system. A monitoring system can, for example, be designed to be transparent to the occupant of the dwelling and, therefore, such a monitoring system can monitor the daily routine of the occupant without the occupant having to interact with the system, such as by pressing buttons, logging onto websites, entering health data, and the like.

A mobile sensor that is moved by a user is utilized in system and method embodiments and used with device embodiments described herein. In some embodiments, for example, a mobile sensor can be worn or carried by an individual (e.g., as a pendant, watch, or other worn accessory, attached to the individual such as on a medical or hospital bracelet, or carried by the individual such as on a key fob, etc.). The mobile sensor can be used to indicate the zone status of the individual (e.g., whether the individual is at home or away from home), therefore, in some embodiments, such mobile sensors can be referred to as home/away sensors.

In various embodiments, signals received by one or more wireless access points of a wireless network from a mobile sensor can be an indication that the individual possessing the home/away sensor is present in a monitoring zone (e.g. in a "home" state) based on a comparison to a zone map (e.g., inside zone). Similarly, in various embodiments, signals received by one or more wireless access points from a mobile sensor can be used as an indicator that the individual possessing the home/away sensor is not present in a monitoring zone (e.g. in an "away" state) based on a comparison to a zone map (e.g., outside zone). Such a home/away indication can, for example, be used as an activation indicator for an accompanying monitoring system to allow other functions of the monitoring system to be active or as a sensor to indicate to the system that the individual is home or away which can, for example, be used to verify if other sensor activations or a lack thereof is cause for initiating an alarm or status check, among other benefits.

In various embodiments, the mobile sensor can be used to indicate that an individual to be monitored is present or not present within the monitoring zone. As part of a monitoring system, if the individual is not present, then this can be communicated to the monitoring system associated with the position system to suppress a false alert initiation based upon the absence of sensor activations during a prolonged period, among other benefits.

In various embodiments, the mobile sensor can be checked to identify if it is present in the monitoring zone. If it is not present, then the position detection system can cycle after a time period has passed and recheck to see if the sensor is present at that later time. In some embodiments, the system can report an error after the system has accomplished a number of such cycles and rechecks. Additional system checks, including mobile sensor checks can be accomplished at this point in the process as well as at other points in the process.

In some embodiments, if the mobile sensor is not working for some reason (e.g., the individual fell and the mobile sensor broke during the fall), this can be indicated to the position detection system because no signals are being received by the wireless access points or weak or uncharacteristic signals are being received by the wireless access points. In such instances, a logic component of an accompanying monitoring system can use other sensors to cross-check whether the mobile sensor position detection is correct.

For example, as part of a monitoring system, the exit door sensors of the dwelling can be checked to see if the individual activated them, indicating that the individual did leave the dwelling. If no exit sensors were activated, then there is a likelihood that the individual is still within the dwelling.

This can be helpful in instances where the monitoring system is not receiving sensor activations and therefore the system is wondering if the individual is incapacitated or otherwise not able to move. By cross-checking with the door sensors, a false alarm, for example, may be avoided.

In various embodiments, a zone map is used to make the home/away determination with regard to the location of the mobile sensor, for example, based on a comparison of one or more of the signals from the mobile sensor and the zone map. In one or more embodiments, a zone map can be created can be created by mapping the locations of a number of fixed sensors in a zone and the signal strengths of a number of communications between the fixed sensors and at least two wireless access points. The signal strengths of a number of the communications between the number of wireless access points and a mobile sensor can be determined and then compared to the with the zone map to determine the mobile sensor's position in relation to the zone.

In various embodiments, the communications between the fixed and mobile sensors and the wireless access points can be via a wireless network such as a Wireless Local Area Network (WLAN). For example, the communication between the fixed and mobile sensors and the wireless access point can be on one or more channels on a WLAN (e.g., WiFi network) network.

In some such embodiments, the system can use groups of sensors for creating a number of zone maps, for example, for different areas of a building that can be used for determining the position of the mobile sensor. Each of the zone maps could be considered "home" for the mobile sensor, therefore, when the comparison of the mobile sensor communications with the zone maps indicates a presence in a zone, the mobile sensor can, for example, be deemed in a "home" state, in some such embodiments.

For instance, sensors can be grouped by in a variety of ways. For example, sensor can be grouped by types of sensors (e.g., motion, water monitoring, contact, etc.), position within the building (e.g., hallway, kitchen, bathroom, bedroom, etc.), or by daily activity (e.g., eating, transfer, waking, etc.). These sensor groups can, in some embodiments, be grouped together to create a zone, where the signals from these sensors to the wireless access points are recorded and used to create a zone map.

In various embodiments, the zone maps containing the signal strength data from the sensor's in the zone can be periodically updated. For example, a time period can be set where the sensors in the zone will send a signal that is received by the wireless access points and sent to a data center once every time period.

The time period can, for instance, be 1 hour, among other time periods, for regular maintenance and updating of the zone map. In some embodiments, the time period can also be adjusted to go into "rapid learn mode" when the zone map needs to relearned or updated, where the time period could be shorted to 2 minutes, among other time periods. In various embodiments, the "rapid learn mode" can be used for a 2 hour interval, among other time intervals, until an adequate data set is available to create the zone map.

In some such embodiments, the updating of the zone map can be used to determine whether a sensor is malfunctioning and/or can allow the zone map to be used for home/away determinations despite, for instance, a malfunctioning sensor. For example, if a sensor is not sending a signal and/or if a wireless access point is not transmitting signals, this can be indicated on the zone map and/or in mobile sensor's signal, therefore the comparison may not be skewed based upon such issues, in some embodiments.

The Figures herein follow a numbering convention in which the first digit or digits correspond to the drawing Figure number and the remaining digits identify an element or component in the drawing. Similar elements or components between different Figures may be identified by the use of similar digits.

Figure 2:
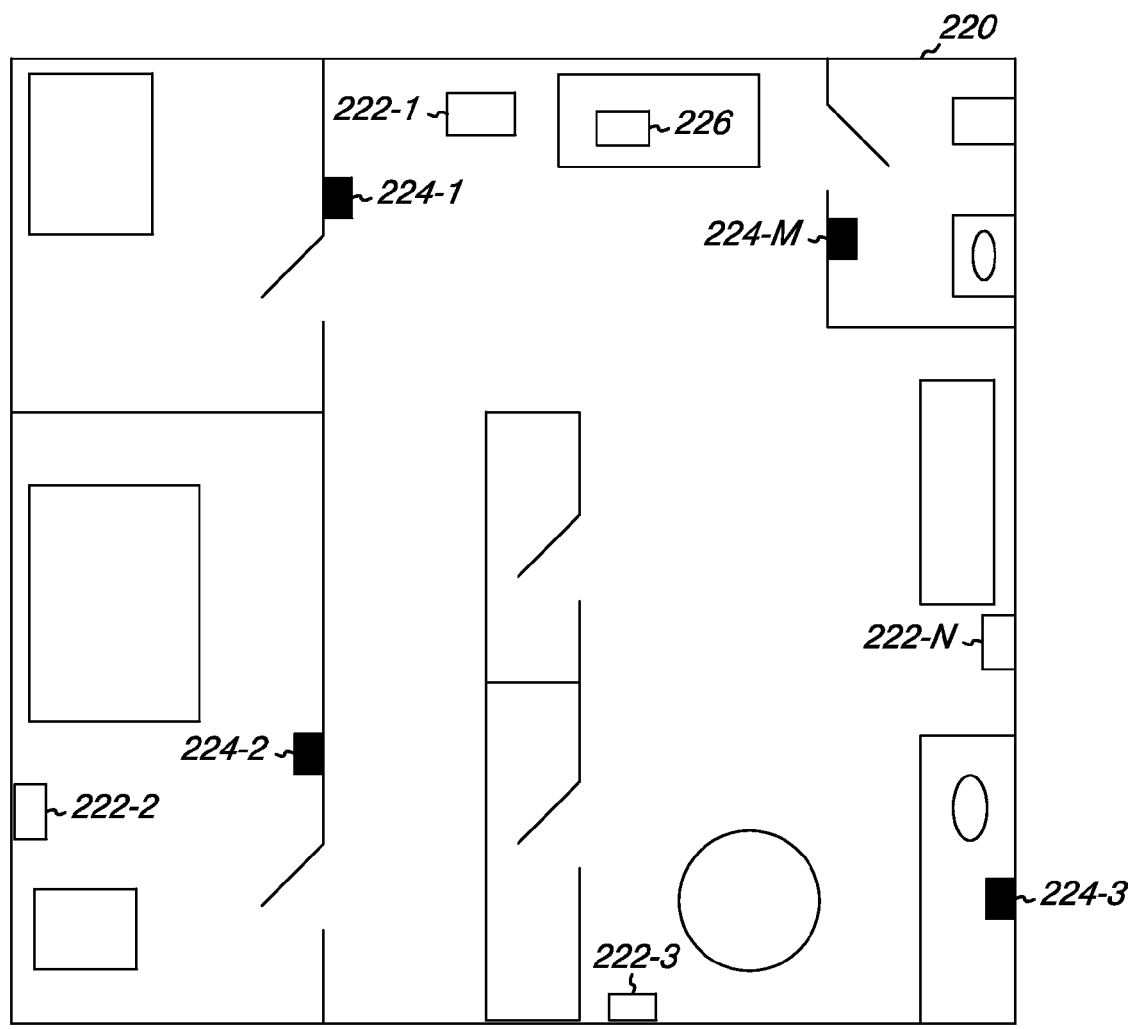
FIG. 2 illustrates an embodiment of a system for detecting the position of an individual implemented in a dwelling according to the present disclosure.

For example, 104 may reference element "20" in FIG. 1, and a similar element may be referenced as 220 in FIG. 2. As will be appreciated, elements shown in the various embodiments herein can be added, exchanged, and/or eliminated so as to provide any number of additional embodiments of the system. In addition, the elements shown in the various embodiments are not necessarily to scale. Also, the designators "N" and "M" are used to indicate that a number of the associated elements can be included in the embodiment of the Figure.

FIG. 1 illustrates an embodiment of a system for monitoring the position of an individual according to the present disclosure. In the system for monitoring the position of an individual 100, a data center 110 is used to collect data from the various components for the system 100.

In some embodiments, the data center 110 can include a processor 112, memory 114, a transceiver 116, and a power supply 118. The transceiver 116 can be used to receive data from the various components via a wired connection and/or via a wireless network, such as a WLAN, among other wireless network types, and can be a transmitter and receiver in some embodiments. The data that is received by the data center 110 can be stored in the memory 114 and the processor 112 can be used to perform the task to monitor the position of the individual by executing a number of executable instructions which can, for example, be stored in the memory, among other places on the network.

In some embodiments, the processor functionality of monitoring the position of the individual can be provided by a logic device, such as hardware based logic rather than a processor. For example, as defined herein executable instructions can be executable by devices having software, firmware, and/or solid-state components.

In various embodiments, the system 100 defines a monitoring zone 120. The various components in the monitoring zone can be part of a wireless network, such as a WLAN, and these components can be coupled to the data center 110 via a wired connection and/or through a wireless network.

The monitoring zone 120 can include in individual's home, a portion of an individual's home, a dwelling, a hospital, and/or any area that is desired to be monitored. The monitoring zone 120 can include a number of Fixed sensors 124-1, 124-2, 124-3, and 124-M.

The fixed sensors can be placed in any desired position throughout the monitoring zone and can be part of larger monitoring system that includes the system for monitoring the position of an individual. The fixed sensors 124-1, 124-2, 124-3, and 124-M can be motion sensors, temperature sensors, pressure sensors, and/or light sensors, among many other types of sensors utilized in the art for monitoring individuals.

In various embodiments, the fixed sensors 124-1, 124-2, 124-3, and 124-M can generate signals in a binary (e.g., on/off) fashion, such that the sensor generates a signal when the object being sensed changes state. For example, with respect to a sensor on a door, one type of sensor that can be provided can operate such that when the door is closed, no signal is generated, but when the door is opened, a signal is generated.

However, embodiments of the invention are not limited to the use of on/off type sensors and can include various types of sensing devices, including ones whose signal strengths scale to the size of the activation parameter, such as temperature, weight, or touch. The fixed sensors can also generate signal(s) when desired as part of a regular time interval and/or also as part of irregular time intervals that are used during special circumstances, such as after a power outage and/or battery replacement, among other special circumstances.

For example, in various embodiments, the fixed sensors can be of various types, for instance, types of sensors include: sensors to indicate the opening and closing of a door or drawer; sensors to indicate the movement of objects such as shades or blinds; current and/or voltage sensors to monitor appliances, lights, wells, etc.; pressure or fluid flow sensors to indicate the turning on and off of water; temperature sensors to indicate that the furnace is on or off; force sensors such as strain gauge sensors to sense an individual walking over a pad, sitting in a chair, or lying in bed; motion sensors to sense the motion of objects within the dwelling; and alert switches/buttons to signal an emergency or client input such as a cancellation request.

As illustrated in the embodiment of FIG. 1, in various embodiments, the monitoring zone 120 can include a number wireless access points 122-1, 122-2, 122-3, and 122-N. The wireless access points 122-1 122-2, 122-3, and 122-N can provide wireless access to a wireless network, such as a WLAN, by transferring signals on one or more channels between various components of the wireless network, such as sensors, base stations, and/or computing devices, among other components.

The wireless access points 122-1, 122-2, 122-3, and 122-N communicate via signals with the fixed sensors 124-1, 124-2, 124-3, and 124-M. The signal strength of these communications is recorded by the data center and is used to create the zone maps that trend the signal strength of a given fixed sensor with a given wireless access point in the zone.

In the embodiment of FIG. 1, the system 100 can also include a mobile sensor 126. The mobile sensor 126 can be part of a portable device, for example, a pendant or other item that can be worn or carried by a user of the system.

The mobile nature of the mobile sensor 126 allows the sensor to move with the user wherever the user goes.

For example, in some embodiments, a pendant having a sensor can be carried or worn by the client and can include a button or switch, for example, that can be used to send a signal to other components of a wireless network. Portable devices can be any type of device that is portable and that can provide the described functionalities.

Examples can include basic devices that have a sensor and the capability to provide power to the sensor and/or complex devices having multiple functions. Examples of complex portable devices can include mobile phones and portable computing devices, such as PDA's and the like.

In various embodiments, the mobile sensor 126 can also communicate via wireless signals with the wireless access points 122-1, 122-2, 122-3, and 122-N. These signals can be communicated to the data center 110, where they are recorded and analyzed through a comparison with the zone maps that are stored in memory 114 of the data center 110.

In some embodiments, multiple signals from the mobile sensor 126 are communicated to and recorded by the data center 110 to allow for a more accurate comparison to the zone map and in turn a more accurate determination of the position of the mobile sensor in relation to the wireless access points in the zone. For example, in some embodiments, five signals can be sent from the mobile sensor 126 the wireless access points and recorded at the data center 110 when a position determination is being made.

FIG. 2 illustrates an embodiment of a system for monitoring the position of an individual implemented in a dwelling according to the present disclosure. In the embodiment of FIG. 2, the system for monitoring the position of an individual includes a user's home 220. In the embodiment of FIG. 2, the home 220 is also the monitoring zone. In various embodiments, multiple monitoring zones can be used, where a home is split into a number of zones. Also, in various embodiments, the monitoring zone can include an apartment, a group of buildings, and/or any area desired to be monitored.

In the embodiments of FIG. 2, the monitoring zone includes four fixed sensors, 224-1, 224-2, 224-3, and 224-M. In various embodiments, any number of fixed sensors can be used.

The sensors can be of various types. For example, fixed sensor 224-1 can be a motion sensor that is located in the living room area of the user's home. Fixed sensor 224-2 can be a motion sensor located in the bedroom used to detect movements from the bed and the opening of the bedroom door. Fixed sensor 224-3 can be a light sensor that can sense the turning on and off of the light switch in the kitchen. Fixed sensor 224-M can be a pressure sensor that can detect the flow of water in the bathroom tub. The embodiments of the present disclosure are not limited to these types of sensors or to any specific locations within a dwelling.

For example, in various embodiments, any combination of sensor types and positions can be part of the monitoring zone and position detection system. These sensors 224-1, 224-2, 224-3, and 224-M can communicate with the wireless access points 222-1, 222-2, 222-3, and 222-N in the user's home 220.

The wireless access points 222-1, 222-2, 222-3, and 222-N are used to wirelessly link the various components of the position detection system (e.g., sensors) to other components of the position detection system (e.g., other sensors and/or computing devices, such as a data center). In some embodiments multiple wireless access points are used in a monitoring zone to increase the likelihood of having a viable signal that is communicated by reducing the distance the signal has to travel with in the monitoring zone and also to have redundancy within the position detection system in case a wireless access point becomes inoperable.

In the embodiment of FIG. 2, a mobile sensor 226 is worn by a user that is sitting on the couch in the living room of the user's home 220. As discussed above, the mobile sensor 226 can be part of a pendant that is worn by the user. For example, the pendant can be worn as a necklace, on the user's belt, and/or in the user's pocket, among any other attachment mechanism.

The pendant can accompany the user wherever the user travels. As such, the embodiments of the present disclosure can be used to determine the position of the user in relation to the monitoring zone based on the signals that the mobile sensor 226 in the pendant communicates to the wireless network.

Figure 3:
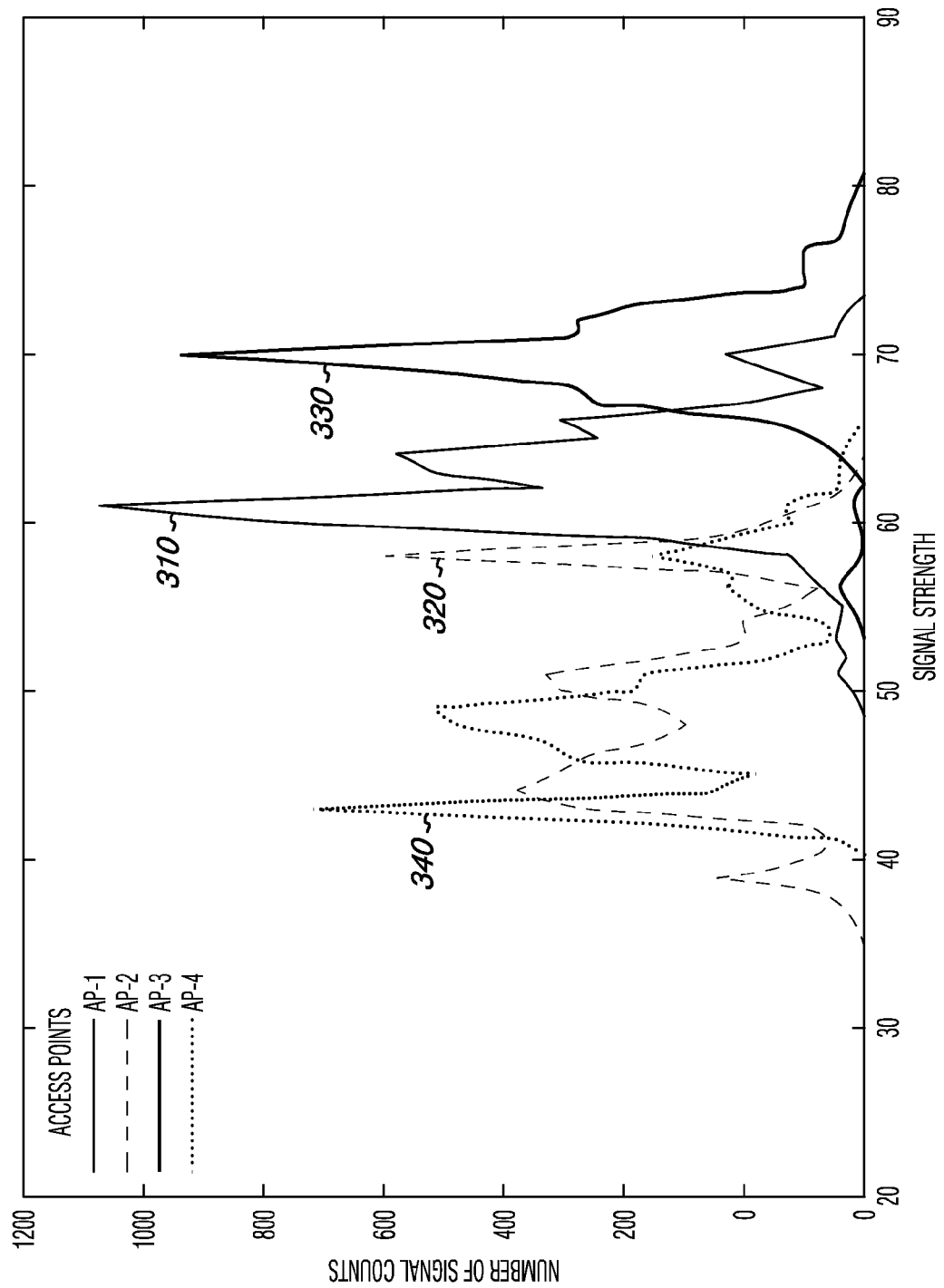
FIG. 3 illustrates an embodiment of the signal strength of wireless communication between a number of sensors and a number of wireless access points in a system for monitoring the position of an individual implemented in a dwelling according to the present disclosure.

FIG. 3 illustrates an embodiment of the signal strengths of wireless communications between a number of sensors and a number of wireless access points in a system for monitoring the position of an individual implemented in a dwelling according to the present disclosure. In the embodiment of FIG. 3, the graph illustrates the number of times a given signal strength was reported for each fixed sensor that is communicating with the wireless access points of the system.

The x-axis of the graph indicates the strength of the signals on a scale of 0 to 100. For example, wireless access point 1 (AP-1) had a minimum reported signal strength of approximately 48 on the left end of the curve 310 and a maximum reported signal strength of approximately 73 on the right end of the curve 310. The y-axis of the graph indicates the number of times a given signal strength magnitude was recorded at each wireless access point. For example, AP-1 reported receiving a signal with the strength of approximately 61 approximately 1100 times, indicated by the peak of curve 310.

In the embodiment illustrated in FIG. 3, each of the curves on the graph indicate the total number of signals received at the wireless access point for all of the sensors in a monitoring zone. In the embodiment of FIG. 3, the monitoring zone includes four wireless access points, which represent the wireless access points 122-1, 122-2, 122-3, 122-N and 222-1, 222-2, 222-3, 222-N from. FIGS. 1 and 2 respectively.

Each wireless access point has a curve on the graph to indicate the strengths of the signals that the wireless access point received during a certain time period. The curves in FIG. 3 include the combined number of counts for signals for each fixed sensor of the monitoring zone. In various embodiments, any type and number of sensors can be used in the monitoring zone. In the embodiment of FIG. 3, four sensors are used in the monitoring zone, and the zone maps for each individual sensor are indicated in FIGS. 4A-4D, discussed below.

In the embodiment of FIG. 3, the graph includes curves 310, 320, 330, and 340. Each curve in FIG. 3 illustrates the number of signal counts each of the four wireless access points received from the four sensors. Curve 310 illustrates the total number of signal counts received by wireless access point 1 (AP-1), which corresponds to wireless access point 122-1 from FIG. 1 and 222-1 from FIG. 2, from all of the sensors in the zone.

In the embodiment of FIG. 3, curve 320 illustrates the total number of signal counts received by wireless access point 2 (AP-2), which corresponds to wireless access point 122-2 from FIG. 1 and 222-2 from FIG. 2, from all of the sensors in the zone. Curve 330 illustrates the total number of signal counts received by wireless access point 3 (AP-3), which corresponds to wireless access point 122-3 from FIG. 1 and 222-3 from FIG. 2, from all of the sensors in the zone. Curve 340 illustrates the total number of signal counts received by wireless access point 4 (AP-4), which corresponds to wireless access point 122-N from FIG. 1 and 222-N from FIG. 2, from all of the sensors in the zone.

In the embodiment of FIG. 3, the graph illustrates the zone map for a monitoring zone for a given time interval. The zone map is then, for example, stored at the data center and can be used to compare to the signals communicated between the mobile sensor and the wireless access points.

The comparison can, for example, include the data set of signal strength counts for the mobile sensor signals at each wireless access point to the data set of the signal strength counts for the fixed sensor signals at each wireless access point. If the data points are similar, the conclusion can be made that the mobile sensor is in the zone and more precisely, in some embodiments, the approximate position of the mobile sensor in relation to one of the fixed sensors or a number of fixed sensors in the monitoring zone. In some embodiments, a Bayesian filter can be applied to the data set of signal strength counts for the mobile sensor signals to produce a probable position of the mobile pendant and/or a confidence factor for that probable position. Such methodology may increase the certainty of the position estimate, in various embodiments.

In some embodiments, the zone map can be updated at various intervals, such as every day, month, and/or year, among other time intervals. The zone map can be updated, for example, to include new positions for one or more of the fixed sensors and/or any new fixed sensors that may be added to the monitoring zone, or the removal of any sensors from the zone.

In some embodiments, the data forming the zone map can be represented as the relative difference between signal strength recordings of the fixed sensors. In some instances, this may aid in the speed at which the information can produce an estimate, among other benefits.

Also, in some embodiments, the data forming the zone map can include the ratios of the signal strengths for the fixed sensors. Similarly, this may aid, in some instances, in the speed at which the information can produce an estimate, among other benefits.

FIGS. 4A-4D illustrate an embodiment of the signal strengths of wireless communications between a sensor and a number of wireless access points in a system for monitoring the position of an individual implemented in a dwelling according to the present disclosure.

Figure 4A:
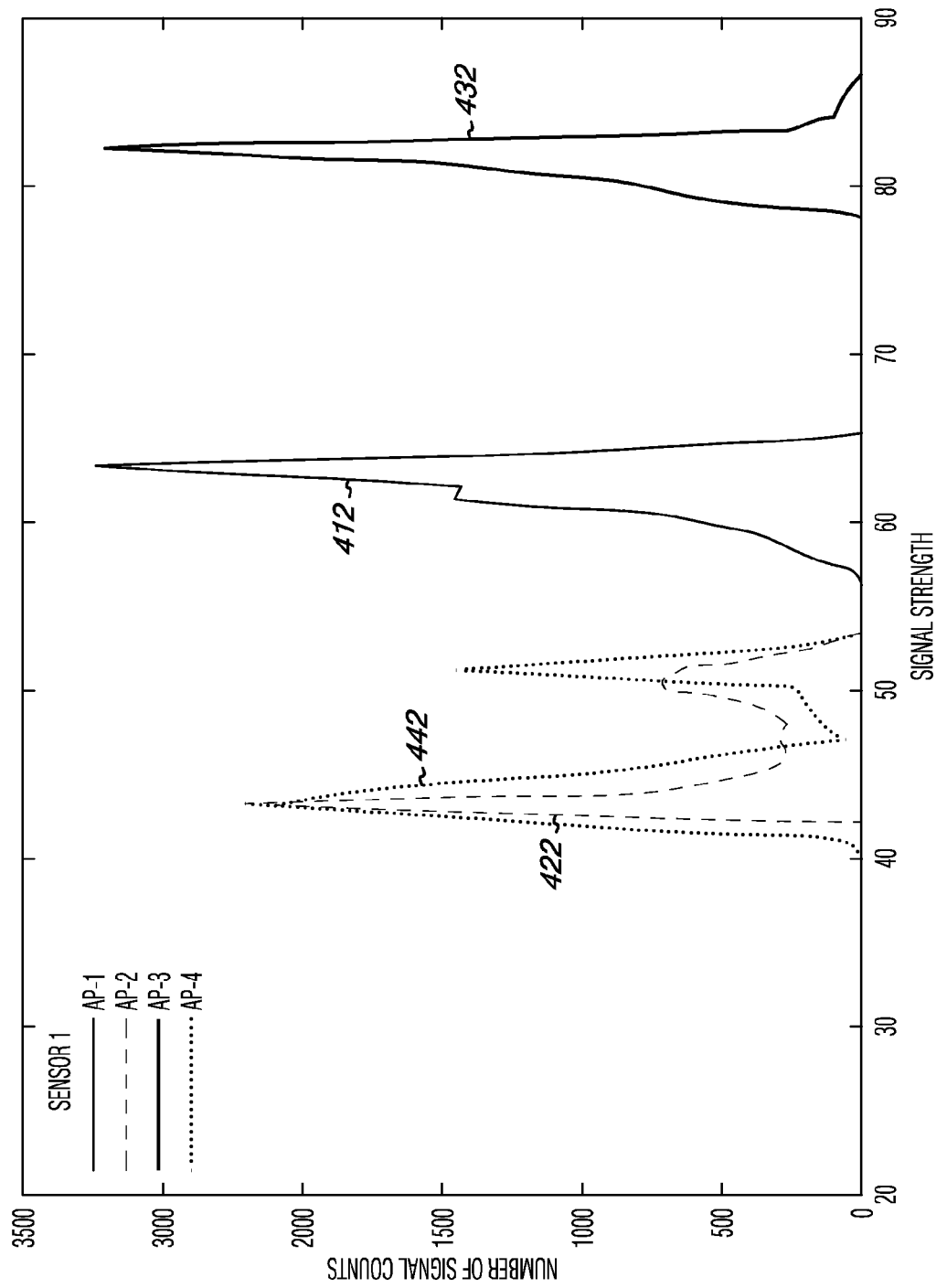
FIGS. 4A-4D illustrate an embodiment of the signal strength of wireless communication between a sensor and a number of wireless access points in a system for monitoring the position of an individual implemented in a dwelling according to the present disclosure.

In the embodiment illustrated in FIG. 4A, each of the curves on the graph indicate the total number of signals received at the wireless access point for the sensor 224-1 (sensor 1) from FIG. 2 in the monitoring zone. The zone map for sensor 224-1 in FIG. 4A indicates a high signal count with a peak of over 2000 counts for three of the four wireless access points (i.e., AP-1, AP-2, AP-3, and AP-4).

This indicates that large a number of signals were communicated from the sensor to the wireless access points and data associated with this sensor provides a great amount of statistically significant data to the zone map. Also, in some embodiments, the zone map for this sensor could be used to indicate a proximate local relationship to the mobile sensor if a signal map for the mobile sensor is similar to the zone map of FIG. 4A.

In the embodiment of FIG. 4A, the graph includes curves 412, 422 432, and 442. Each curve in FIG. 4A illustrates the number of signal counts each wireless access point received from sensor 1, which corresponds to sensor 124-1 from FIG. 1 and sensor 224-1 from FIG. 2.

Curve 412 illustrates the total number of signal counts received by wireless access point 1 (AP-1), which corresponds to wireless access point 122-1 from FIG. 1 and 222-1 from FIG. 2, from sensor 1 in the zone. Curve 422 illustrates the total number of signal counts received by wireless access point 2 (AP-2), which corresponds to wireless access point 122-2 from FIG. 1 and 222-2 from FIG. 2, from sensor 1 in the zone.

Curve 432 illustrates the total number of signal counts received by wireless access point 3 (AP-3), which corresponds to wireless access point 122-3 from FIG. 1 and 222-3 from FIG. 2, from sensor 1 in the zone. Curve 442 illustrates the total number of signal counts received by wireless access point 4 (AP-4), which corresponds to wireless access point 122-N from FIG. 1 and 222-N from FIG. 2, from sensor 1 in the zone.

Figure 4B:
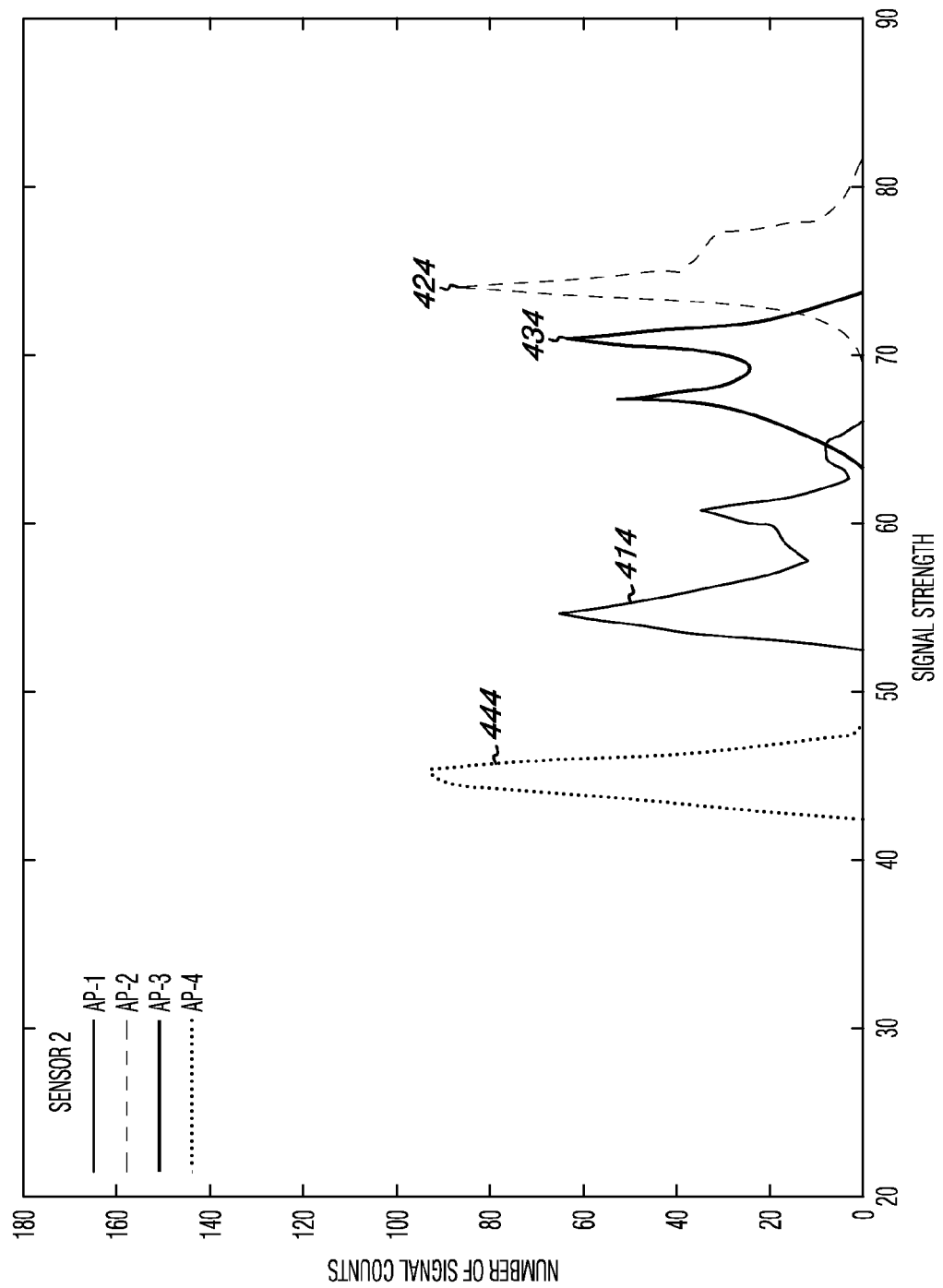

In the embodiment illustrated in FIG. 4B, each of the curves on the graph indicate the total number of signals received at the wireless access point for the sensor 224-2 from FIG. 2 in the monitoring zone. The zone map for sensor 224-2 (sensor 2) in FIG. 4B indicates a signal count with a peak of less than 200 counts for the four wireless access points. This indicates that small a number of signals were communicated from the sensor to the wireless access points and data associated and, therefore, sensor 2 may not be functioning properly or the time interval of the data collected to create this zone map was shorter in relation to other time intervals.

In the embodiment of FIG. 4B, the graph includes curves 414, 424, 434, and 444. Each curve in FIG. 4B illustrates the number of signal counts each wireless access point received from sensor 2, which corresponds to sensor 124-2 from FIG. 1 and sensor 224-2 from FIG. 2.

Curve 414 illustrates the total number of signal counts received by wireless access point 1 (AP-1), which corresponds to wireless access point 122-1 from FIG. 1 and 222-1 from FIG. 2, from sensor 2 in the zone. Curve 424 illustrates the total number of signal counts received by wireless access point 2 (AP-2), which corresponds to wireless access point 122-2 from FIG. 1 and 222-2 from FIG. 2, from sensor 2 in the zone.

Curve 434 illustrates the total number of signal counts received by wireless access point 3 (AP-3), which corresponds to wireless access point 122-3 from FIG. 1 and 222-3 from FIG. 2, from sensor 2 in the zone. Curve 444 illustrates the total number of signal counts received by wireless access point 4 (AP-4), which corresponds to wireless access point 122-N from FIG. 1 and 222-N from FIG. 2, from sensor 2 in the zone.

Figure 4C:
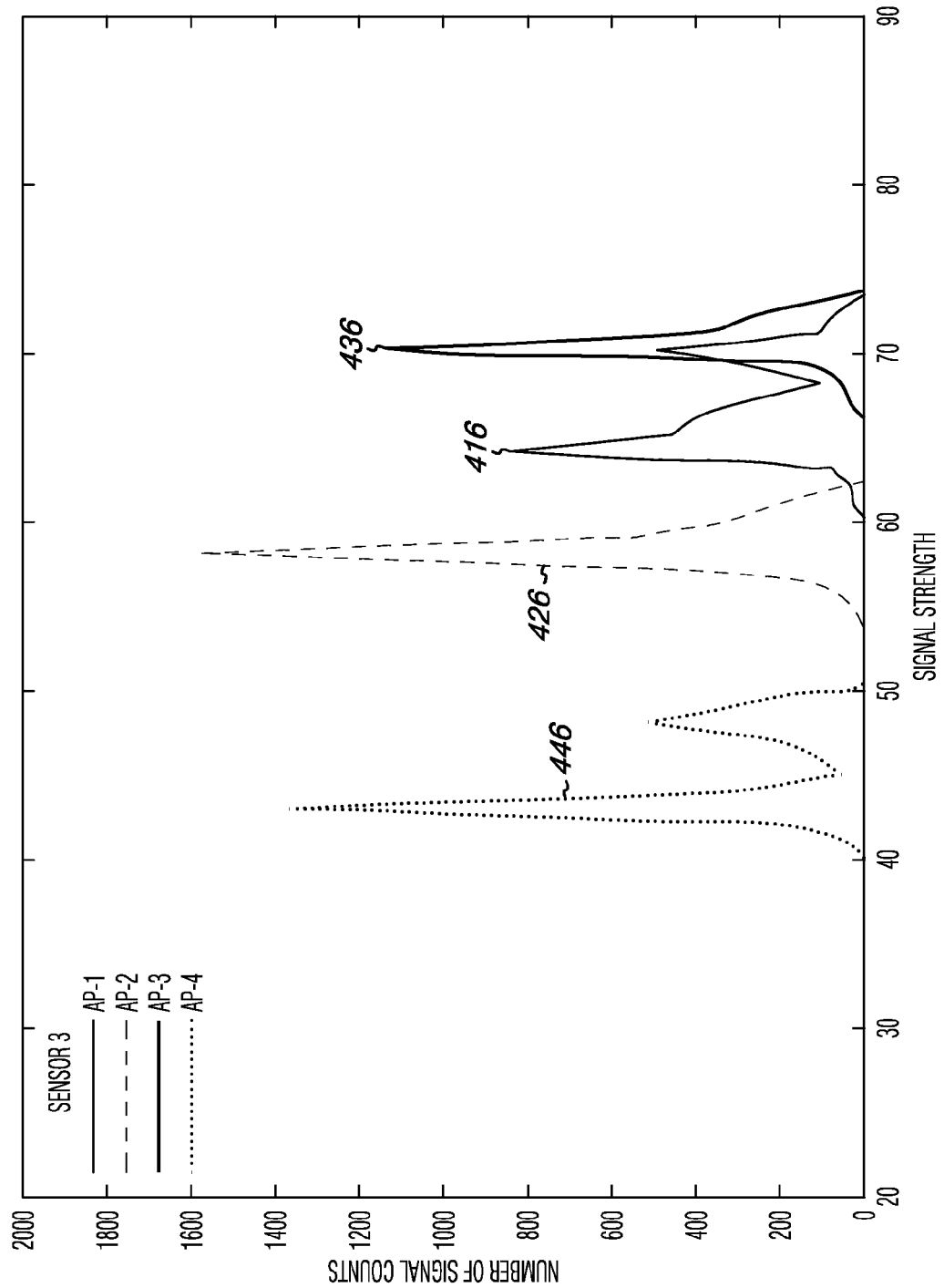

In the embodiment illustrated in FIG. 4C, each of the curves on the graph indicate the total number of signals received at the wireless access point for the sensor 224-3 (sensor 3) from FIG. 2 in the monitoring zone. The zone map for sensor 224-3 in FIG. 4C indicates a high signal count with a peak of over 1000 counts for the four wireless access points.

This indicates that large a number of signals were communicated from the sensor to the wireless access points and data associated with this sensor provides a great amount of statistically significant data to the zone map. Also, the zone map for this sensor indicates that the signal strength distribution for each wireless access point is tight, only overlapping slightly.

This can indicate that the sensor is located in a way that signals communicated between the sensor and the wireless access point provides a unique range of signal strengths at each wireless access point. This trend for the sensor's signal strengths could be used to indicate a proximate local relationship to the mobile sensor if a signal map for the mobile sensor is similar to the curve for one of the wireless access points in FIG. 4C.

In the embodiment of FIG. 4C, the graph includes curves 416, 426, 436, and 446. Each curve in FIG. 4C illustrates the number of signal counts each wireless access point received from sensor 3, which corresponds to sensor 124-3 from FIG. 1 and sensor 224-3 from FIG. 2.

Curve 416 illustrates the total number of signal counts received by wireless access point 1 (AP-1), which corresponds to wireless access point 122-1 from FIG. 1 and 222-1 from FIG. 2, from sensor 3 in the zone. Curve 426 illustrates the total number of signal counts received by wireless access point 2 (AP-2), which corresponds to wireless access point 122-2 from FIG. 1 and 222-2 from FIG. 2, from sensor 3 in the zone.

Curve 436 illustrates the total number of signal counts received by wireless access point 3 (AP-3), which corresponds to wireless access point 122-3 from FIG. 1 and 222-3 from FIG. 2, from sensor 3 in the zone. Curve 446 illustrates the total number of signal counts received by wireless access point 4 (AP-4), which corresponds to wireless access point 122-N from FIG. 1 and 222-N from FIG. 2, from sensor 3 in the zone.

Figure 4D:
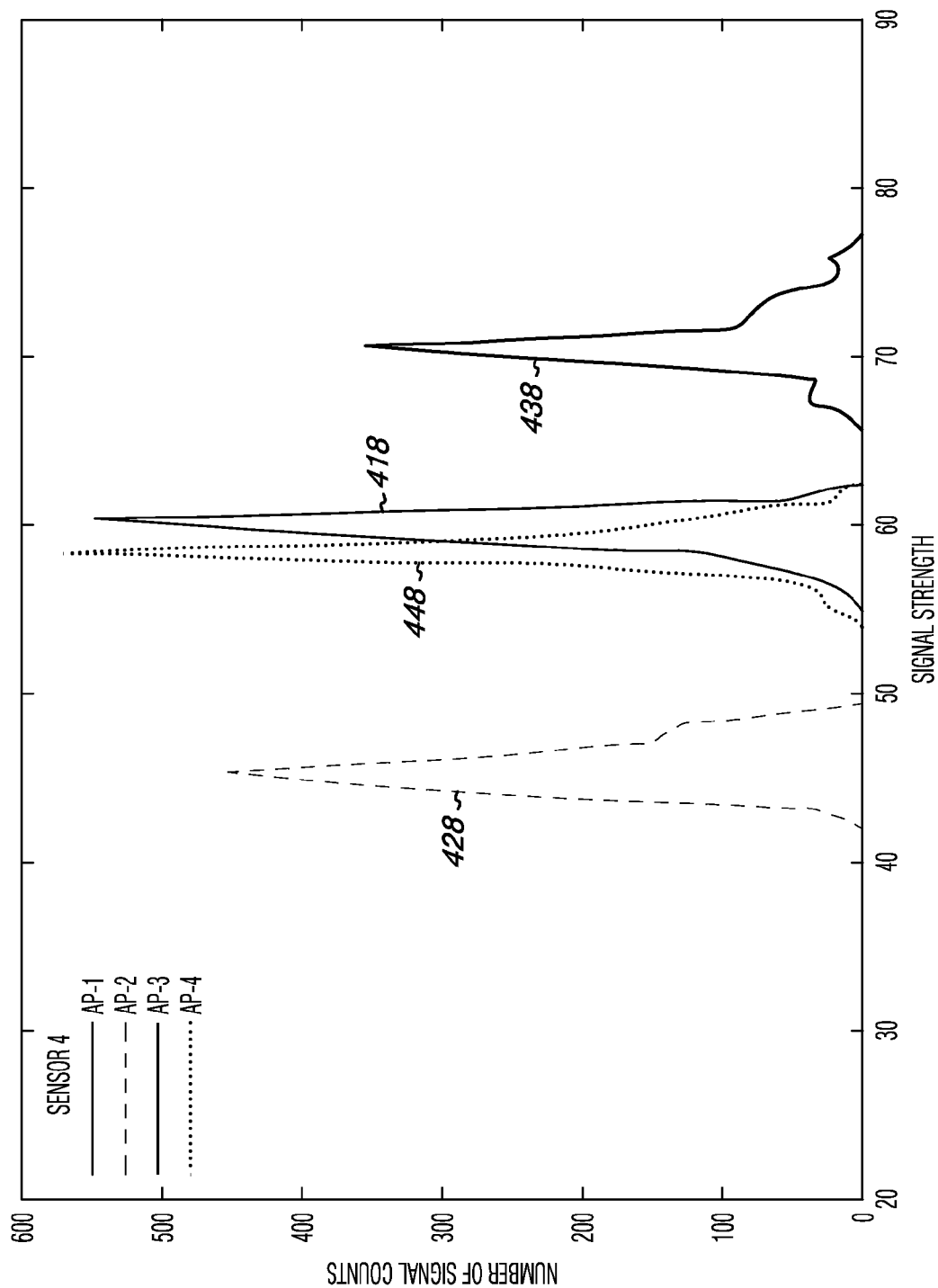

In the embodiment illustrated in FIG. 4D, each of the curves on the graph indicate the total number of signals received at the wireless access point for the sensor 224-M from FIG. 2 in the monitoring zone. The zone map for sensor 224-M in FIG. 4D indicates a signal count with a peak of less than 600 counts for the four wireless access points.

Also, the zone map for this sensor indicates that the signal strength distribution for each wireless access point is tight, with most of the counts occurring in a narrow range of signal strengths. This can indicate that the sensor is located in a way that provides consistent signal strength to each wireless access point. This feature of the sensor could be used to indicate that the signal strength from the sensor to the wireless access points does not vary over magnitude ranges and the data has a lower variance indicating more precise data despite the lower number of signal counts when compared to the graphs in FIGS. 4A and 4C.

In the embodiment of FIG. 4D, the graph includes curves 418, 428, 438, and 448. Each curve in FIG. 4D illustrates the number of signal counts each wireless access point received from sensor 4, which corresponds to sensor 124-M from FIG. 1 and sensor 224-M from FIG. 2.

Curve 418 illustrates the total number of signal counts received by wireless access point 1 (AP-1), which corresponds to wireless access point 122-1 from FIG. 1 and 222-1 from FIG. 2, from sensor 4 in the zone. Curve 428 illustrates the total number of signal counts received by wireless access point 2 (AP-2), which corresponds to wireless access point 122-2 from FIG. 1 and 222-2 from FIG. 2, from sensor 4 in the zone.

Curve 438 illustrates the total number of signal counts received by wireless access point 3 (AP-3), which corresponds to wireless access point 122-3 from FIG. 1 and 222-3 from FIG. 2, from sensor 4 in the zone. Curve 448 illustrates the total number of signal counts received by wireless access point 4 (AP-4), which corresponds to wireless access point 122-N from FIG. 1 and 222-N from FIG. 2, from sensor 4 in the zone.

Figure 5:
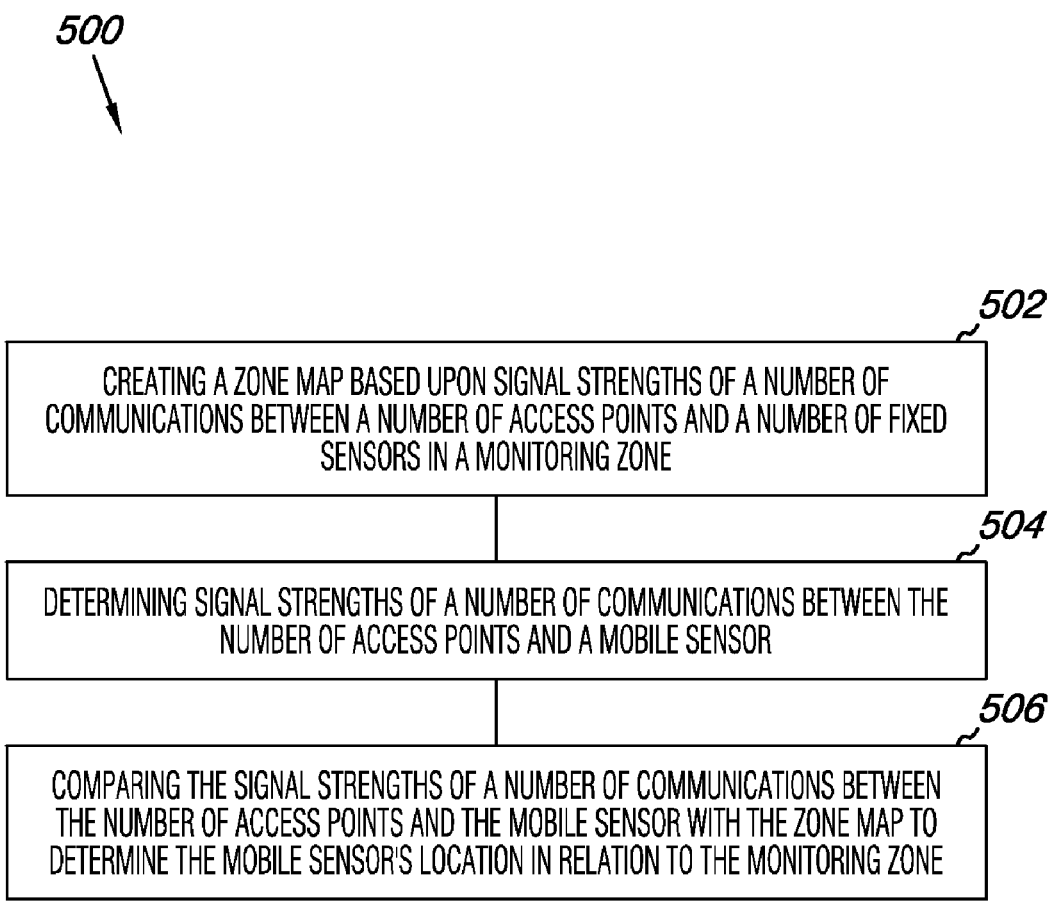
FIG. 5 is a block diagram illustrating a method for detecting the position of an individual according to the present disclosure.

FIG. 5 is a block diagram illustrating a method for monitoring the position of an individual according to an embodiment of the present disclosure. In the embodiment of FIG. 5, the method for monitoring the position of an individual 500 includes creating a zone map based upon signal strengths of a number of communications between a number of wireless access points and a number of fixed sensors forming a zone, at block 502.

As illustrated in FIG. 5, method embodiments can also include determining signal strengths of a number of communications between the number of wireless access points and a mobile sensor, at block 504. Method embodiments can also include comparing the signal strengths of the number of communications between the number of wireless access points and the mobile sensor with the zone map to determine the mobile sensor's position in relation to the zone, at block 506.

Although specific embodiments have been illustrated and described herein, those of ordinary skill in the art will appreciate that an arrangement calculated to achieve the same techniques can be substituted for the specific embodiments shown. As one of ordinary skill in the art will appreciate upon reading this disclosure, various embodiments of the invention can be performed in one or more devices, device types, and system environments including networked environments.

Combination of the above embodiments, and other embodiments not specifically described herein will be apparent to those of skill in the art upon reviewing the above description. The scope of the various embodiments of the disclosure includes other applications in which the above structures and methods can be used. Therefore, the scope of various embodiments of the disclosure should be determined with reference to the appended claims, along with the full range of equivalents to which such claims are entitled.

In the foregoing Detailed Description, various features may have been grouped together in a single embodiment for the purpose of streamlining the disclosure. This method of disclosure is not to be interpreted as reflecting an intention that the embodiments of the invention require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for detecting a position of an individual, comprising:
    creating a zone map by mapping locations of a number of fixed sensors in a zone and signal strengths of a first number of communications between the fixed sensors and a number of wireless access points;
    determining signal strength values of a number of communications between the number of wireless access points and a mobile sensor; and
    comparing the signal strength values of the number of communications between at least two of the number of wireless access points and the mobile sensor with the zone map to determine the mobile sensor's position in relation to the zone.

2. The method of claim 1, wherein creating the zone map includes updating one or more signal strength values based on an evaluation of a second number of communications between the at least two wireless access points and at least one of the number of fixed sensors in the zone at multiple periodic intervals.

3. The method of claim 2, wherein creating the zone map includes updating one or more signal strength values based on an evaluation of the second number of communications between the at least two wireless access points and at least one of the number of fixed sensors in the zone wherein the number or position of the wireless access points or fixed sensors has changed between two periodic intervals.

4. The method of claim 2, wherein updating one or more signal strength values occurs at a periodic interval selected from the range of intervals from 1 to 4 minutes for a period selected from a range of 2 to 4 hours.

5. The method of claim 1, wherein the first number of communications between the at least two wireless access points and the number of fixed sensors in the zone and the number of communications between the at least two of the number of wireless access points and the mobile sensor are on one or more discrete communication channels.

6. The method of claim 1, wherein determining signal strength values of the number of communications between the number of wireless access points and the mobile sensor occurs during a period selected from a range of 5 to 15 minutes.

7. A method for detecting a position of an individual, comprising:
    scanning one or more communication channels, utilized by at least two wireless access points, with one or more fixed sensors, wherein at least one of the one or more fixed sensors records the signal strength of a signal received during communication with each of the wireless access points;
    transmitting data representing the recorded signal strength from the one or more fixed sensors to a data center;
    scanning one or more channels for a number of wireless access points with a mobile sensor, wherein the mobile sensor records the signal strength received during communication with each of the number of wireless access points;
    transmitting data representing the recorded signal strength from the mobile sensor to the data center; and
    analyzing the data representing the recorded signal strength from the one or more fixed sensors and the data representing the recorded signal strength from the mobile sensor to determine the position of the mobile sensor in relation the one or more fixed sensors.

8. The method of claim 7, wherein the method includes applying a Bayesian filter when analyzing the data representing the recorded signal strength from at least one of the fixed sensors and the data representing the recorded signal strength from the mobile sensor to determine the position of the mobile sensor in relation to the at least one of the fixed sensors.

9. The method of claim 7, wherein the method includes recording the mobile sensor signal strength received during communication with at least one of the wireless access points multiple times and analyzing the multiple recorded signal strengths to determine the position of the mobile sensor in relation to the one or more fixed sensors.

10. The method of claim 7, wherein analyzing the data representing the recorded signal strength from the one or more fixed sensors and the data representing the recorded signal strength from the mobile sensor to determine the position of the mobile sensor in relation the one or more fixed sensors includes analyzing a relative difference between signal strength recordings of the one or more fixed sensors.

11. The method of claim 7, wherein analyzing the data representing the recorded signal strength from the one or more fixed sensors and the data representing the recorded signal strength from the mobile sensor to determine the position of the mobile sensor in relation the one or more fixed sensors includes analyzing a ratio of the signal strength recording of one fixed sensor to another one of the one or more fixed sensors.

12. The method of claim 7, wherein analyzing the data representing the recorded signal strength from the one or more fixed sensors and the data representing the recorded signal strength from the mobile sensor to determine the position of the mobile sensor in relation the one or more fixed sensors includes identifying a wireless access point that a particular sensor was associated with when a particular signal strength was recorded.

13. A system for detecting a position of an individual, comprising:
- a number of fixed sensors located in a zone;
- a mobile sensor that is moved by a user;
- a data center; and
- a number of wireless access points,
  - wherein the wireless access points provide wireless access to a network that includes the number of fixed sensors, the mobile sensor, the number of wireless access points, and the data center, and
  - wherein the fixed sensors and the mobile sensor periodically report the signal strength of communications between at least two wireless access points and at least one of the number of fixed sensors to the data center to determine the position of the mobile sensor in relation to the number of fixed sensors.

14. The system of claim 13, wherein the position of the mobile sensor in relation to the number of fixed sensors is reported to a monitoring individual as a mobile sensor zone status.

15. The system of claim 14, wherein the mobile sensor zone status indicates whether the mobile sensor is located in the zone or located out of the zone.

16. A system for detecting a position of an individual, comprising:
- a number of fixed sensors located in a zone, wherein the zone is defined by an area less than or equal to a range of wireless communication for all of the number of fixed sensors;
- a mobile sensor that is moved by a user, wherein the mobile sensor transmits one or more wireless signals to a wireless network;
- at least two wireless access points, where the wireless access points provide wireless access to the wireless network; and
- a data center, wherein the data center includes executable instructions to create a zone map of signal strengths communicated by the number of fixed sensors based on data received via the wireless network and wherein the data center determines the position of the mobile sensor based upon the zone map and mobile sensor signal strength data sent from the mobile sensor to the data center on the wireless network via the at least two wireless access points.

17. The system of claim 16, wherein the executable instructions are executable by a device selected from the group including devices having one or more software, firmware, or solid-state components.

18. The system of claim 16, wherein the fixed sensors of the wireless network are used for monitoring activity of an individual and used to initiate an alert based on a set of rules associated with activations of the fixed sensors.

19. The system of claim 16, wherein a Bayesian filter is used on the mobile sensor signal strength data to determine the position of the mobile sensor based upon the zone map and mobile sensor signal strength data.

20. The system of claim 16, wherein the zone map is updated with the signal strengths of a number of communications between the wireless access points and the number of fixed sensors located in the zone.

* * * * *